United States Patent [19]

Iannella

[11] Patent Number: 4,933,490

[45] Date of Patent: Jun. 12, 1990

[54] PROCESS FOR THE PREPARATION OF L(−)CARNITINE HYDROCHLORIDE AND OF L(−)CARNITINE INNER SALT

[75] Inventor: Vincenzo Iannella, Milan, Italy

[73] Assignee: ISOM S.p.A., Milan, Italy

[21] Appl. No.: 99,633

[22] Filed: Sep. 22, 1987

Related U.S. Application Data

[63] Continuation of Ser. No. 666,839, Oct. 31, 1984, abandoned.

[30] Foreign Application Priority Data

Nov. 2, 1983 [IT] Italy ............................... 23563 A/83
Oct. 22, 1984 [IT] Italy ............................... 49045 A/84

[51] Int. Cl.$^5$ ..................... C07C 51/43; C07C 53/126
[52] U.S. Cl. .................................... 562/401; 562/402; 562/554; 562/567

[58] Field of Search ................... 260/501.13; 562/402, 562/554, 401, 567

[56] References Cited

U.S. PATENT DOCUMENTS

| | | | |
|---|---|---|---|
| 3,096,368 | 7/1963 | Binon et al. ........................ | 562/554 |
| 3,135,788 | 6/1964 | Noguchi et al. ............... | 260/501.13 |
| 3,151,149 | 9/1964 | Strack et al. ................... | 260/501.13 |

FOREIGN PATENT DOCUMENTS 93347 10/1972 German Democratic Rep. .

*Primary Examiner*—Joseph E. Evans
*Attorney, Agent, or Firm*—Alexis Barron

[57] ABSTRACT

The invention refers to a process for the preparation of L(−)carnitine by using dibenzoyl-D(31 )tartaric acid and crystallizating the relative salt at low temperature.

13 Claims, No Drawings

PROCESS FOR THE PREPARATION OF L(−)CARNITINE HYDROCHLORIDE AND OF L(−)CARNITINE INNER SALT

This is a continuation of co-pending application Ser. No. 666,839 filed on Oct. 31, 1984, now abandoned.

The present invention refers to a process which can be easily carried out industrially for the production both of L(−)carnitine hydrochloride and of L(−)carnitine inner salt, starting from D,L-carnitine, by using dibenzoyl-D(−)tartaric acid.

Processes for the resolution of D,L-carnitine by means of optically active organic acids have been already described. Namely, East Germany Patent No. 93347 claims a process for the preparation of D,L-carnitine in its optical isomers by using, moreover, dibenzoyl-D(−)tartaric acid.

The process disclosed and claimed in said patent has however a series of serious drawbacks, which make it absolutely unsuited for the industrial appliance, and which even on laboratory scale give L(−)carnitine in very low yields, and with an unacceptable content of impurities (detected by a specific rotatory power remarkably lower than that of the pure isomer).

Example 3 of said patent (concerning precisely the separation of dibenzoyl-D-tartrates of L-carnitine and D-carnitine) comprises the following steps:

(a) obtaining a first portion of L-carnitine dibenzoyl-D-tartrate by crystallization of the diastereo isomeric salts mixture from methanol at +4° C.;

(b) recrystallization of said portion from methanol obtaining a L-carnitine dibenzoyl-D-tartrate with $[\alpha]_D = -95.2°$ and yield of 62%;

(c) evaporation to dryness of the mother solutions collected from steps (a) and (b);

(d) recrystallization, from ethanol/methanol, of the residue of (c) obtaining part of D-carnitine dibenzoyl-D-tartrate;

(e) a not otherwise specified fractional crystallization of the "residual mother solutions", with recovery of further L-carnitine dibenzoyl-D-tartrate (whose rotatory power is not reported); the total yield of this salt should therefore raise to 78%.

At this point—for the recovery of L-carnitine from the dibenzoyl-D-tartrate—the patent refers to the Example 10, comprising:

(f) suspension of the salt in water and extraction with ether of most (91%) dibenzoyl-D-tartaric acid;

(g) elimination of the residual 9% of said acid by passing the aqueous solution on anion-exchange resins;

(h) evaporation to dryness of the water solution, obtaining "pure" L-carnitine (the characteristic data are not specified) with a 82.5% yield based on the salt and with a total yield, therefore, of 64.3%.

As one can understand, the process is definitely complex because it requires: (1) use of two different crystallization solvents for carnitine dibenzoyl-tartrate; (2) an extraction with ether (solvent whose hazard is known); (3) elution on an exchange resin column; (4) evaporation of an highly diluted L-carnitine water solution.

All these drawbacks could perhaps be considered as tolerable taking into account the total yields, reported in the Example 3 of said patent, of the yield (64.3%) of L-carnitine, whose rotatory power—as already said—is not however reported.

However, if the examples 3 and 10 of the DDR patent No. 93347 are carried out exactly as reported, the reality appears to be completely different. The first fraction of L-carnitine dibenzoyl-D-tartrate is obtained, at the end of steps (a) and (b), in a yield of 47%, and with an $[\alpha]_D = -93°$; in order to bring this value to an acceptable limit, −95°, two recrystallizations are necessary, further reducing the yield; attempts to obtain a second fraction of salt having a reasonable purity degree systematically failed; lastly, also steps (f) - (g) - (h) occur so as the total yield of L-carnitine does not exceed, if all goes well, 29% of the theoric value. Not only: the final product so obtained has $[\alpha]_D = -18°$, unacceptable from the marketing point of view, and which can be increased up to good levels only with operations further reducing the process total yields.

It is thus clear that the teaching of DDR patent No. 93347 allows to obtain L(−)carnitine neither with acceptable yields nor purities, nor with an industrially applicable process.

It is also to be kept in mind that said patent does not disclose anything about the preparation conditions of the starting D,L-carnitine (which is presumed anhydrous) from the respective hydrochloride, which is the normally available product. Said conditions are other than indifferent, if one considers the high hygroscopicity of carnitine, and the consequent difficulties of obtaining it in anhydrous form starting exactly from the salts thereof.

It has now been unexpectedly found that L(−)carnitine dibenzoyl-D(−)tartrate can be easily separated, in high yields and with a very high purity degree, from its diastereoisomeric salt, D(+)carnitine dibenzoyl-D(−)tartrate, if the mixture of the two salts is crystallized from methanol at temperatures not higher than −10° C. It was noticed that even at slightly higher temperatures, i.e. from −5° and −4° C., the separation of the diastereoisomer salts occur with much less satisfactory results, both for the yields (decreasing of 40–50%) and for the optical purity (the L(−)carnitine dibenzoyl-(D)(−)tartrate has, in this case, $[\alpha]_D^{20} = -93.2°$).

An object of the present invention is therefore provided by a process for the separation L(−)carnitine dibenzoyl-D(−)tartrate from D(+)carnitine dibenzoyl-D(−)tartrate by means of crystallization from methanol at temperatures not higher than −10° C.

Said crystallization is carried out in the substantial absence of water.

This is achieved—starting from commercially available D,L-carnitine hydrochloride—by treating said hydrochloride first with an alkaline hydroxide in substantially stoichiometric amounts, in alcoholic solvents not necessarily anhydrous and then with a substantially equimolar amount of dibenzoyl-D(−)tartaric acid, optionally humid. The precipitate, comprising the diastereoisomer salts mixture, is then dried and crystallized.

According to a preferred embodiment of the invention, nevertheless, D,L-carnitine hydrochloride (i.e. the raw material commercially available) is reacted with sodium alcoxide (preferably methoxide) in methanol and—after filtration of sodium chloride formed as a by-product—with dibenzoyl-D-tartaric acid in substantially equimolar amount under heating; a solution is therefore obtained which, by cooling to a temperature not higher than −10° C., gives directly a precipitate of L(−)carnitine dibenzoyl-D(−)tartrate already remarkably pure, from which it is possible to obtain, by recrystallization from methanol, said salt with a yield of 70–80%, and with $[\alpha]_D^{20}$ ranging from −95° and −96°.

It has been moreover found that from the salt so obtained, the L-carnitine hydrochloride is obtained quickly and in an almost quantitative yield by suspending the salt in an inert solvent (such as acetone, methylethylketone, methylisobutylketone, ethyl acetate) and adding thereto anhydrous HCl in stoichiometric amount or in slight excess with respect to said amount.

According to the process of the present invention it is therefore possible to obtain L(−)carnitine hydrochloride from commercial D,L-carnitine hydrochloride through very simple operative steps (without using crystallization solvents different from time to time, ether extractions, resins elutions or evaporation to dryness of water solutions). As far as the preferred embodiment is concerned, said operative steps can be so summarized:

(a) preparing an anhydrous methanolic solution of D,L-carnitine inner salt starting from D,L-carnitine hydrochloride and sodium methoxide in methanol;

(b) adding dibenzoyl-D(−)tartaric acid to said solution, with contemporaneous precipitation (at temperatures of −10° C. or lower) of L(−)carnitine dibenzoyl-D(−)tartrate already remarkably pure;

(c) recrystallization (simple or double) the latter, always from methanol, at temperatures of −10° C. or lower;

(d) obtaining L(−)carnitine hydrochloride, always in the absence of water, by addition of aqueous HCl to the suspension of dibenzoyl-D(−)tartrate obtained in (c), in aprotic solvents.

Whenever convenient, the L(−)carnitine dibenzoyl-D(−)tartrate can be transformed into the D(−)carnitine inner salt instead of the corresponding hydrochloride. For this purpose the dibenzoyl-D(−)tartrate is suspended in a biphasic system formed by water and by a water immiscible or poorly miscible solvent (preferably ethyl acetate) and treated with sulphuric acid: the dibenzoyl-D(−)tartaric acid goes in the organic phase while calcium or barium oxide or carbonate in stoichiometric amount is added to the aqueous phase, containing L(−)carnitine sulphate.

After filtration of $CaSO_4$ or $BaSO_4$, the L-carnitine inner salt is recovered from the aqueous solution by evaporation and treating the residue with a nonsolvent.

Of course, the dibenzoyl-D(−)tartaric acid is recovered from the different solutions containing it, by evaporation of solvents, preceded—in the case of methanolic mother solutions—by acidification with mineral acids. The recovery yield is as a whole higher than 90°.

The invention will be further illustrated by the following non limiting examples.

EXAMPLE 1

L(−)Carnitine dibenzoyl-D(−)tartrate

125 Grams of ground NaOH are introduced under stirring in 1500 ml of methanol, followed by 600 g of D,L-carnitine hydrochloride. The sodium chloride is pump-filtered, washed with little methanol and 1146 g of dibenzoyl-D(−)tartaric acid monohydrate are added to the methanolic solution.

The mixture is heated to about 40° C., then about 60% of methanol is distilled off under reduced pressure, 1200 ml of water are added and the distillation is continued up to complete elimination of methanol, which is recovered in amounts of 80-85%.

The crystalline precipitate obtained, formed by L(−)carnitine and D(+)carnitine dibenzoyl-D(−)tartrates, is pump-filtered, washed with water and dried under vacuum. 1480 Grams of dry salts, which are dissolved under heating in 1630 ml of methanol, are obtained. The solution is cooled under stirring to temperatures ranging from −12° to −10° C., and the precipitate is pump-filtered, washed with about 100 ml of methanol, cooled to −12° C., and recrystallized according to the same procedures, first from 600 and then from 500 ml of methanol. The final precipitate is dried.

In this way 576 g (74%) of L(−)carnitine dibenzoyl-D(−)tartrate are obtained, m.p. 147°-150° C., $[\alpha]_D^{20} = -95.4$ (C=10%; $CH_3OH$).

EXAMPLE 2

L(−)Carnitine dibenzoyl-D(−)tartrate

A solution of 164 g of sodium methoxide dissolved in 400 ml of methanol is added dropwise to a suspension of 600 g of D,L-carnitine hydrochloride in 1000 ml of methanol. The suspension is stirred for 45', then the formed sodium chloride is filtered and 1120 g of anhydrous dibenzoyl-D(−)tartaric acid are added to the methanolic solution of D,L-carnitine inner salt.

The mixture is heated to complete solution, then cooled to a temperature ranging from −10° to −12° C., stirred at this temperature for 5 hours and filtered, washing with little cold methanol.

The obtained salt, without being dried, is recrystallized in the same temperature conditions, first from 600 ml and then from 500 ml of methanol. After drying, 588 g (73.3%) of L(−)carnitine dibenzoyl-D(−)tartrate, melting at 146°-150° C. and $[\alpha]_D^{20} = -95.50°$ (C=10%; $CH_3OH$), are obtained.

EXAMPLE 3 (comparative)

Operating exactly as described in Example 1, but at temperatures of −4° up to −5° C., instead of −12° to −10° C., 343 g of L-carnitine dibenzoyl-D(−)tartrate having $[\alpha]_D^{20} = -93.2°$ C., are recovered. The L-carnitine hydrochloride obtainable (according to the subsequent Example 4) from this salt shows $[\alpha]_D^{20} = -18.8°$.

EXAMPLE 4

L(−)Carnitine hydrochloride

41 Grams of gaseous hydrochloric acid are bubbled, at room temperature, into a suspension of 550 g of L(−)carnitine dibenzoyl-D(−)tartrate in 1400 ml of acetone. The suspension is then stirred for 1 hour and filtered. 1200 Grams (95.5%) of L(−)carnitine hydrochloride having $[\alpha]_D^{20} = -21°$ (C=3; $H_2O$); m.p. 138°-139° C., are obtained. After evaporation of acetone the dibenzoyl-D(−)tartaric acid is quantitatively recovered.

EXAMPLE 5

L(−)carnitine inner salt

550 Grams of L(−)carnitine are added to a mixture of 1000 ml of ethyl acetate, 300 ml of water and 55 g of 98% sulphuric acid, with stirring till complete solution. After separation of the two layers, 40 g of calcium oxide and 9 g of calcium carbonate are added to the aqueous phase and the mixture is stirred until a pH=6.5-7.0 is obtained. After pumpfiltration, the aqueous solution is evaporated under vacuum, the residue is treated with ethanol and evaporated to dryness again. A residue is obtained, which is treated with ethanol and acetone to give L(−)carnitine inner salt as a white crystalline solid.

After filtration and drying, 165 g of L(−)carnitine inner salt, having $[\alpha]_D^{20} = -28.5°$ (C=1; H$_2$O) and with water content lower than 3% (yield=94%), are obtained. The dibenzoyl-D(−)tartaric acid is recovered in substantially quantitative yield by evaporating ethyl acetate.

I claim:

1. In a process for preparing a hydrochloride or inner salt of L(−)carnitine by fractional crystallization of D,L-carnitine dibenzoyl-D(−)tartrates in methanolic solution, the improvement comprising effecting said crystallization at a temperature of not higher than −10° C.

2. A process according to claim 1 wherein said D,L-carnitine dibenzoyl-D(−)tartrates is formed in aqueous medium and dried before said crystallization.

3. A process according to claim 1 wherein said methanolic solution is formed from substantially equimolar ratios of D,L-carnitine hydrochloride and dibenzoyl-D(−)tartaric acid and a sodium alcoxide.

4. A process according to claim 3 wherein said sodium alcoxide is sodium methoxide.

5. A process according to claim 1, 2, 3 or 4 wherein L(−)carnitine dibenzoyl-D(−)tartrate formed from said crystallization is converted to said hydrochloride by suspending said tartrate in an aprotic solvent in the presence of a substantially equimolar amount of anhydrous HCl.

6. A process according to claim 5 wherein said aprotic solvent is selected in the group consisting of acetone, methylethylketone, methylisopropylketone and ethyl acetate.

7. A process according to claim 1, 2, 3 or 4 wherein L(−)carnitine dibenzoyl-D(−)tartrate formed from said crystallization is converted to said inner salt by suspending said tartrate in a biphasic system comprising water and a water immiscible or poorly water miscible solvent, forming in said system an aqueous phase containing L(−)carnitine sulfate by adding thereto sulfuric acid in a substantially equimolar amount, separating the phases, forming calcium sulfate or barium sulfate by treating said aqueous phase containing said L(−)carnitine sulphate with calcium or barium oxide or carbonate in equimolar amounts, and recovering said inner salt by separating therefrom CaSO$_4$ or BaSO$_4$ and water.

8. A process according to claim 7 in which ethyl acetate is used as said solvent.

9. A process for preparing L(−)carnitine in the form of a hydrochloride or of an inner salt from D,L-carnitine hydrochloride and with the use of dibenzoyl-D(−)tartaric acid comprising:
(a) treating a methanolic solution in D,L-carnitine hydrochloride with a substantially equimolar amount of sodium methoxide, thereby forming sodium chloride;
(b) separating sodium chloride from said solution and then adding thereto a substantially equimolar amount of dibenzoyl-D(−)tartaric acid, thereby forming a solution of diastereoisomer salts;
(c) forming solid L(−)carnitine dibenzoyl-D-(−)tartrate by cooling said solution of diastereoisomer salts to a temperature not higher than −10° C.; and
(d) crystallizing from methanol at a temperature not higher than −10° C. in high purity form L(−)carnitine dibenzoyl-D(−)tartrate.

10. A process according to claim 9, including forming L-carnitine hydrochloride by suspending said tartrate of (d) above in an aprotic solvent in the presence of a substantially equimolar amount of anhydrous HCl.

11. A process according to claim 9 including forming said inner salt by forming a suspension of said tartrate of (d) above in a water/hydroimmiscible solvent biphasic system and in the presence of a substantially equivalent amount of H$_2$SO$_4$, separating the aqueous phase of said system, precipitating from said separated phase sulphate as calcium or barium sulfate and evaporating to dryness the aqueous solution from which said calcium or barium sulphate has been separated.

12. In a process for preparing a hydrochloride or inner salt of L(−)carnitine by fractional crystallization of D,L-carnitine dibenzoyl-D(−)tartrates in methanolic solution and by the use of D,L-carnitine hydrochloride, the improvement comprising: (A) forming a methoxide by reacting methanol and an alkaline hydroxide, the amount of said hydroxide being substantially stoichiometrically equivalent to that of said D,L-carnitine hydrochloride; (B) reacting said methoxide with siad D,L-carnitine hydrochloride to form D,L-carnitine inner salt in methanolic solution; (C) adding to said solution dibenzoyl-D(−)tartaric acid in an amount substantially equimolar relative to the amount of said inner salt and forming a methanolic solution thereof; and (D) crystallizing from said methanolic solution L(−)carnitine dibenzoyl-D(−)tartrate by cooling said methanolic solution to a temperature of −10° C. or lower.

13. In a process for preparing a hydrochloride or inner salt of L(−)carnitine by fractional crystallization of D,L-carnitine dibenzoyl-D(−)tartrates in methanolic solution and by the use of D,L-carnitine hydrochloride, the improvement comprising: (A) forming a methoxide by reacting methanol and an alkaline hydroxide, the amount of said hydroxide being substantially stoichiometrically equivalent to that of said D,L-carnitine hydrochloride; (B) reacting said methoxide with said D,L-carnitine hydrochloride to form D,L-carnitine inner salt in methanolic solution; (C) adding to said solution dibenzoyl-D(−)tartaric acid in an amount substantially equimolar relative to the amount of said inner salt and forming a methanolic solution thereof; (D) separating from a methanolic solution solid L(−)carnitine dibenzoyl-D(−)tartrate by cooling to a temperature of −10° C. or lower; (E) crystallizing from methanol at a temperature of not higher than −10° C. the separated L(−)carnitine dibenzoyl-D(−)tartrate; and (F) thereafter converting said crystallized L(−)carnitine dibenzoyl-D(−)tartrate into L(−)carnitine hydrochloride or into L(−)carnitine inner salt.

* * * * *